(12) United States Patent
Ferracani et al.

(10) Patent No.: US 8,985,121 B2
(45) Date of Patent: Mar. 24, 2015

(54) METHOD AND DEVICE FOR VALVE REPAIR

(75) Inventors: Enrique Ferracani, Buenos Aires (AR); Wolfgang Neuberger, Dubai (AE)

(73) Assignee: Biolitec Pharma Marketing Ltd., F.T. Labuan (MY)

( * ) Notice: Subject to any disclaimer, the term of this patent is extended or adjusted under 35 U.S.C. 154(b) by 248 days.

(21) Appl. No.: 13/102,830

(22) Filed: May 6, 2011

(65) Prior Publication Data

US 2011/0213348 A1    Sep. 1, 2011

Related U.S. Application Data

(63) Continuation-in-part of application No. 12/877,721, filed on Sep. 8, 2010, now Pat. No. 8,685,072.

(60) Provisional application No. 61/240,554, filed on Sep. 8, 2009.

(51) Int. Cl.
*A61B 19/00* (2006.01)
*A61B 18/24* (2006.01)
*A61B 18/00* (2006.01)

(52) U.S. Cl.
CPC ....... *A61B 18/24* (2013.01); *A61B 2018/00029* (2013.01); *A61B 2018/00982* (2013.01)
USPC ................... 128/898; 606/7; 606/15; 607/89

(58) Field of Classification Search
USPC ............ 606/3, 7, 13–15; 607/88, 89, 92, 104, 607/105; 128/898
See application file for complete search history.

(56) References Cited

U.S. PATENT DOCUMENTS

| | | | | |
|---|---|---|---|---|
| 6,033,398 A | * | 3/2000 | Farley et al. | 606/27 |
| 2003/0060813 A1 | * | 3/2003 | Loeb et al. | 606/17 |

* cited by examiner

*Primary Examiner* — Ahmed Farah
(74) *Attorney, Agent, or Firm* — Bolesh J. Skutnik; BJ Associates

(57) ABSTRACT

A method and a device for minimally invasive treatment of diseased deep and superficial venous valves are disclosed. Treatment seeks to repair/rejuvenate dysfunctional valve by reducing the circumference of dilated valve rings and by restoring their original shape and function using laser energy to make physical suture points and shrink collagen in selected points. Real time monitoring is by angioscopic view and endovenous echographic control. In a preferred embodiment, system comprises a specific catheter-like device for endovenous insertion that allows for real time view of energy emission and venous surface to be corrected. Catheter flexibility is such that viewing angle and direct energy emission can be oriented properly. Catheter can comprise channels for irrigation or for interchange of laser fibers according to desired irradiation pattern. A preferred embodiment of catheter device also comprises cuffs for temporary occlusion, by inflation and deflation. In preferred embodiments, 1470 nm, 1550 nm or 1900 nm laser energy is applied. This treatment can be applied to venous valves of the deep venous system, as well as valves of the sapheno-femoral junction, terminal valve and pre-terminal valve.

5 Claims, 3 Drawing Sheets

Figure 1:
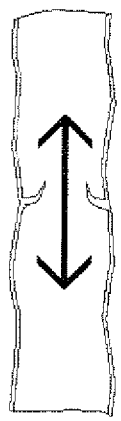 
Fig. 1a             Fig. 1b

METHOD AND DEVICE FOR VALVE REPAIR

CROSS REFERENCE TO PRIORITY APPLICATION

This patent application is a continuation in part and claims priority to, U.S. patent application Ser. No. 12/877,721, filed Sep. 8, 2010 now U.S. Pat. No. 8,685,072, by Wolfgang Neuberger entitled "Device and Method for Vessel Treatment", which in turn was based on U.S. provisional patent application No. 61/240,554, filed Sep. 8, 2009, entitled "Device and Method for Vessel Treatment", each of which is hereby expressly incorporated by reference in its entirety as part of the present disclosure.

BACKGROUND OF THE INVENTION

1. Field of the Invention

The present invention relates to the treatment of vascular disorders and in particular to treatment of blood vessels by using local energy emitting devices and conveying means.

2. Invention Disclosure Statement

The blood vessels are the part of the circulatory system that transport blood throughout the body. There are three major types of blood vessels: the arteries, which carry the blood away from the heart, the capillaries, which enable the actual exchange of water and other substances between the blood and the tissues; and the veins, which carry blood from the capillaries back towards the heart.

The human venous system of the lower limbs consists essentially of the superficial venous system and the deep venous system, both connected by perforating veins. The superficial system comprises the great and the small saphenous veins, while the deep venous system includes the anterior and posterior tibial veins, which converge to form the popliteal vein near the knee. The popliteal vein, in turn, becomes the femoral vein when joined by the small saphenous vein.

The venous system comprises valves, whose main function is to achieve unidirectional blood flow back to the heart. Venous valves are usually bicuspid valves, with each cusp forming a blood reservoir, which force their free surfaces together under retrograde blood pressure. As a consequence, when properly operating, retrograde blood flow is prevented, allowing only antegrade flow to the heart. Thus, under normal conditions venous flow is unidirectional, thanks to correct functioning of the endothelial flaps that oppose reflux. When a valve is absent or becomes incompetent their cusps are unable to seal properly under retrograde pressure gradient, so retrograde blood flow occurs. When retrograde blood flow occurs, pressure increases in the lower venous sections, dilating veins and usually leading to additional valvular failure.

Valve failure, usually referred to as venous insufficiency, is a chronic disease that can lead to skin discoloration, varicose veins, pain, swelling and ulcerations. Varicose veins refer to blood vessels that have become enlarged and twisted and have progressively lost their wall elasticity. Due to the widening of the blood vessels, vein valves cannot be completely closed and veins lose their ability to carry blood back to the heart. This leads to an accumulation of blood inside the vessels, enlarging and twisting the veins even more.

Various methods can be used to eliminate the problem of insufficient veins, including, sclerotherapy, surgery (vein stripping), electro-cautery, and laser treatments. Prior art methods and devices are intended to obliterating and/or eliminating the insufficient veins. This forces the blood to flow through the remaining healthy veins. As a consequence, venous function is not restored in insufficient veins. Instead, these veins are either extracted or closed in order to prevent blood from circulating through them, thus avoiding reflux. The treated veins are no longer capable of conveying blood and generally are no longer present. As a consequence, vein is lost for potential use in future cardiac and other by-pass procedures. Furthermore, recurrence or persistence of varicose veins may occur, particularly if the valvular problem is not resolved. These techniques present another important limitation. They are effective (possible) only for treating superficial veins. They are not indicated for veins at 5 or more cm deep.

Patients with deep venous insufficiency (DVI) must be treated by surgical methods after failure of non-surgical methods. Venous valve reconstruction is a recognized option for treatment of DVI. The concept of remodeling of altered anatomical geometry is applied in a surgical technique called annuplasty, which aims to reduce the circumference of dilated valve rings, thus restoring their shape and function. This concept is accepted for the restoration of valvular defects, cardiac as well as venovascular defects. The restoration techniques of annular dilation, aim to restore the diameter of the circumference by means of internal reduction, thus seeking to achieve proper valve closure and therefore unidirectional valve flow.

Open surgery is one way to repair diseased vessel valves. But it is a costly and risky treatment, and it does not always achieve desired results. Most patients prefer not to undergo such treatment after evaluating cost-benefits.

With the objective of carrying out vascular treatment by restoring venous function of insufficient veins, some approaches have been developed. These techniques are directed towards restoring venous function by making the valve competent.

Two main techniques for restoring venous functionality have been used: implanting a replacement venous valve; and directly treating venous valve incompetence.

In the first case, a valve is implanted inside the vein in order to replace insufficient valve. In general terms, implanted valve can be artificial (made from non-organic materials), a xenograft (from animals) or an autogenous graft (extracted from other site of patient's body). For instance, in U.S. Pat. No. 6,299,637, Shaolian et al. disclose a self-expandable venous valve implant. It comprises a pivotable leaflet and a tubular wire support. Leaflet is positioned in the flow path, for permitting flow in a forward direction and resisting flow in a reverse direction.

In another example, disclosed by Gomez-Jorge et al. in WO00047136A1, a vascular valve prosthesis is formed by suturing a vein valve segment (for example, from a bovine jugular vein) which has been trimmed in order to reduce its thickness.

Venous valve implants present disadvantages. Frequently, and especially in artificial prosthesis, implanted valves require an increased opening pressure. As a consequence, patient condition may further deteriorate, instead of improving. In addition, these surgical treatments require skillful and meticulous techniques, and often patients require multiple interventions. Furthermore, the use of compression stockings is often required even after surgical intervention to ensure relief of symptoms and durability of the operation. Moreover, implant rejection as well as thrombosis may occur in these procedures. Also, procedure is more invasive, more time consuming and its outcome is not as predictable as vein obliteration. Therefore, cost-effectiveness becomes an important drawback.

In the second case, valve competence is intended to be restored by different means. For example, WO09638090A1 discloses an attempt to restore valve competence by reducing insufficient vein diameter. Vein lumen is constricted using an extravascular corrector attached to vein in the region of the incompetent valve. Corrector is made from a resilient shape-memory alloy in order to adapt to vein's structure. This technique is an invasive procedure and presents some drawbacks. Since a foreign body is placed inside organism, there are risks of infection and implant may be encapsulated or even rejected. In addition, material mechanical properties may be altered in time due to biological degradation.

In another approach, described in U.S. Pat. No. 6,322,559 by Daulton et al., vein diameter is also reduced just below an incompetent venous valve, by using a RF heating catheter that constricts the collagen layer. This catheter uses a low-voltage radiofrequency generator to heat expandable electrodes placed on catheter's tip (expandable coil). The surgical procedure consists in a percutaneous insertion of an introducer into the saphenous vein just below the level of the knee, under ultrasound guidance. The electrodes are then expanded to contact the vein wall and heated, during a treatment period of a few minutes. This approach presents some disadvantages. First, it is usually carried out under general or spinal anesthesia, with all the associated risks and complications. Second, since the risk of thrombosis is believed to be substantial with this treatment, low-molecular weight (LMW) heparin is given subcutaneously before and after the procedure, during approximately a week, thus requiring professional attention over this time span. Third, it is a rather long procedure and recurrence is observed after one year, as vein is dilated almost to pre-treatment diameter. Finally, due to catheter's small diameter, it is only appropriate for small veins. If a larger catheter was used, greater veins could be treated, but size of catheter would make it too cumbersome to manipulate.

In order to restore venous function, the controlled shrinkage and strengthening of the vein structure needs to be accomplished. This in turn cannot be accomplished well and in a reliable manner by the relatively unspecific application of RF energy. RF treatment is limited to the reduction of vein diameter near the valve, hoping that consequently, valve will start working properly again, thus preventing reflux. However, if weakened valve is not treated and therefore still present, recurrence may occur.

In an alternative approach, U.S. Patent Publication 2006/0189967A1 by Masotti et al. describes a treatment of varicose veins by means of the recovery of the tone of the venous wall, using a pulsed holmium laser. This is disclosed to be accomplished by causing a hyalinizing sclerosis in the extracellular matrix of the median coat, but preserving tunica intima from thermal damage, using wavelengths between 800 and 2900 nm, preferably 2100 nm (holmium laser). This wavelength is proposed as it is characterized by a high absorption coefficient in water and a low absorption coefficient in hemoglobin. Nevertheless, experience has shown that wavelengths around this value are highly absorbed in blood (probably due to its high content of water), so it is unlikely that radiation would cause its major effect on the tunica media since absorption inside vein lumen will be high. In addition, pulsed holmium lasers usually emit radiation in narrow pulses. Thus, in order to achieve appropriate energy levels for producing certain effects on tissue, laser power must be high. High power radiation applied in short bursts usually creates undesired shockwaves, which in turn will produce undesired and unpredictable effects on tissue. It is well known by those skilled in the art that holmium lasers may not be recommendable for applications in which precise amounts of energy are to be applied and non-linear processes must be avoided. This patent also claims a wavelength range of 800-2900 nm, but effects produced in biological tissues due to the different wavelengths comprised in this range are substantially different. Therefore, it is unlikely that the desired described effect would be achieved with all the wavelengths in the claimed range. For instance, a wavelength of 800 nm is highly absorbed in hemoglobin, thus it is improbable that laser radiation reaches the tunica media without affecting tunica intima.

Size and cost are also important issues to take into account when using holmium lasers. Diode lasers, for example, have numerous advantages over ionic crystal lasers. Among them, are higher output, at reduced dimensions and weight. They also have simpler and smaller air cooling systems. Moreover, being integrated with optical fibers, they have a high reliability and do not need alignment.

Effective and convenient treatment of deep and superficial venous insufficiency due to venous valve incompetence remains elusive. There is thus a need for a minimally invasive vascular treatment that improves on the state of the art, providing a safe and precise vessel function restoration, to recover vessel function. The present invention addresses these needs.

OBJECTIVES AND BRIEF SUMMARY OF THE INVENTION

It is an objective of the present invention to provide an improved minimally invasive method device for vessel treatment.

It is another objective of the present invention to treat diseased vessels by using a localized, directed energy source and conveying means.

It is also an objective of the present invention to treat varicose veins by restoring valve function.

Briefly stated, a method and a device for minimally invasive treatment of diseased deep and superficial venous valves are disclosed. Treatment seeks to repair/rejuvenate dysfunctional valve by reducing the circumference of dilated valve rings and by restoring their original shape and function by using laser energy to make physical suture points and shrink collagen in selected points. Procedure is monitored in real time by angioscopic viewing and endovenous echographic control. In a preferred embodiment, system comprises a specific catheter-like device for endovenous insertion that allows for real time view of energy emission and venous surface to be corrected. Catheter flexibility is such that viewing angle and direct energy emission can be oriented properly. Additionally, catheter can comprise channels for irrigation or for interchange of laser fibers according to desired irradiation pattern. A preferred embodiment of catheter device also comprises cuffs for temporary occlusion, by inflation and deflation. In preferred embodiments, emission of 1470 nm, 1550 nm or 1900 nm laser energy is applied. This treatment can be applied to venous valves of the deep venous system, as well as valves of the sapheno-femoral junction, terminal valve and pre-terminal valve.

The above and other objects, features and advantages of the present invention will become apparent from the following description read in conjunction with the accompanying drawings (in which like reference numbers in different drawings designate the same elements).

BRIEF DESCRIPTION OF FIGURES

FIGS. 1a-ab Show anatomic diagrams of normal and diseased vein valve.

DETAILED DESCRIPTION OF PREFERRED EMBODIMENTS

Present invention seeks to treat patients with deep and superficial venous valves with dilated rings by endoluminally applying laser energy under direct vision to reduce their circumference and restore their original shape and function.

In this device and method for restoring functionality of blood vessels, laser energy is applied to restore vessel functionality by shrinkage and/or strengthening of the vessel structure. Laser radiation is transported via an optical fiber to the site where energy is needed. A mini-endoscope is used to control the process by visual inspection from the inside of the vessel. A radial emitting fiber is used. Energy is applied either from the outside of the vessel, by inserting a device through the skin and tissue or by means of specific radiation absorbers located at suitable positions inside the vessel wall or near the tissue to be treated, thus radiation can then selectively target tagged locations. Energy characteristics and emitting tip configuration makes this invention superior in efficacy and precision in comparison to other mentioned prior art. Some limitations to this earlier approach remain and enhancements are described below.

Present enhanced technique consists in applying laser energy with precision to vein wall and to selected points in valve rings to achieve physical suture points and shrink collagen under continuous angiographic and/or echographic monitoring. Procedure is monitored in real time by angioscopic viewing and/or endovenous echographic control. Catheter device for endovenous insertion allows for real time view of energy emission and venous surface to be corrected. Device may be introduced by echo-guided puncture according to Seldinger technique or by direct venous access.

FIG. 1 shows anatomic diagrams of normal venous function with a healthy vessel valve 1b; and insufficient blood flow due to a diseased vein valve 1a. It can be appreciated that when valve is working properly, blood flow is in one direction. When valve rings are dilated, valve closure is deficient and unidirectional flow is not achieved. Retrograde flow is the main cause for vein insufficiency.

Figures 2, 2A, 2B:
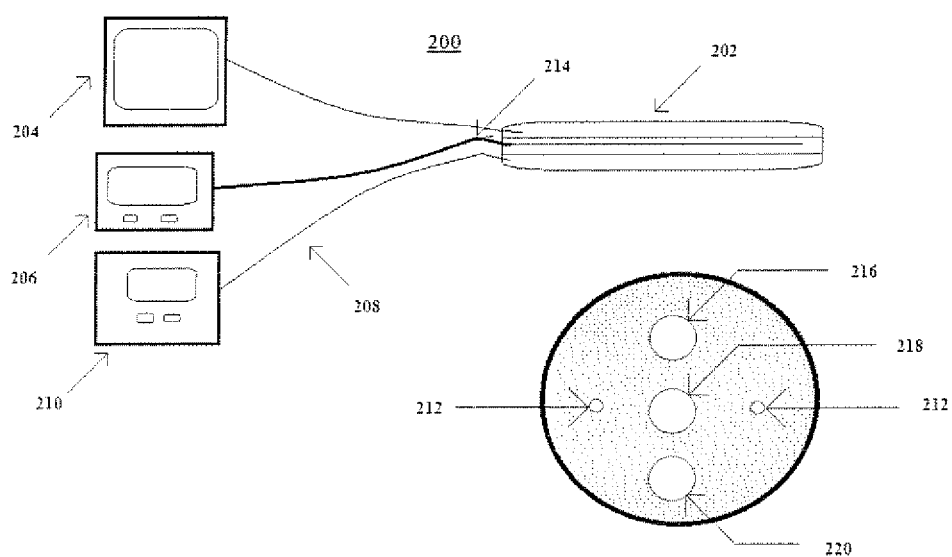
FIGS. 2a-2b show preferred embodiments of main components of present invention.

FIG. 2 depicts longitudinal view 2a of main components of a preferred embodiment of present invention and sagittal view of preferred catheter device 2b. System 200 comprises special endovenous catheter 202, which is inserted into affected vessel under angiographic 204 monitoring through angiographic channel 216 and/or ultrasound 206 monitoring through ultrasound channel 218. Catheter 202 also accepts insertion of optical fiber 208 through fiber channel 220 conveying energy from laser source 210, and other channels such as illumination channels on at least two extremes of device 212 or an irrigation channel (not shown) for clearing the surface of blood. In preferred embodiments, catheter flexibility is such that viewing angle and direct energy emission can be oriented properly. Endovascular access portion of catheter 202 is short and the rest is long enough for connection to surgeon's viewing screen. In another preferred embodiment, catheter includes a 40 MHz ultrasound probe 214 for on-site echocardiographic control. This ultrasound probe is used to measure vessel diameter as well as blood flow before and after treatment. Axial emitting fibers are preferred for lasing points, whereas 360 degree radial emitting fibers are preferred for irradiating pre and post valve vein circumference.

Thus, channel for insertion of optical fiber 208 allows for easy interchange of laser fibers. In a preferred embodiment, emission of 1470 nm laser energy is applied. This wavelength acts directly on the vessel's collagen water content so there is minimum risk of thrombosis, since virtually no bubbles are produced in blood. This treatment can be applied to venous valves of the deep venous system, as well as valves of the sapheno-femoral junction, terminal valve and pre-terminal valve. A preferred embodiment of catheter device also comprises cuffs for temporary occlusion, by inflation and deflation at proximal and distal positions with respect to treated valve. In some cases, treated area requires large quantities of rinsing which cannot be reached by catheter's irrigation channels, thus in another preferred embodiment, an occlusion catheter with an irrigation channel is inserted in opposite direction from treatment catheter for a more exact occlusion and irrigation in vessel-valve area.

Figure 3:
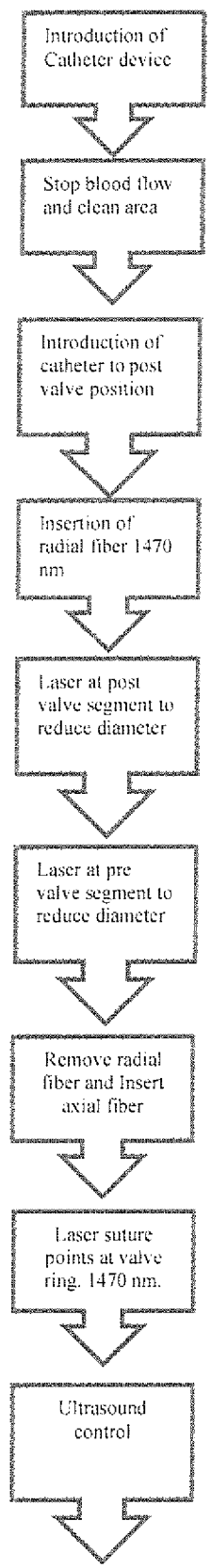
FIG. 3 depicts a preferred embodiment of the present invention describing main procedure steps.

The main steps that comprise a preferred embodiment of this invention are summarized in FIG. 3. First of all, catheter device is inserted by echo-guided puncture according to Seldinger technique or by direct venous access; and advanced through vessel to a position downstream with respect to diseased valve. Distal and proximal cuffs are inflated to stop blood flow in area and a transparent liquid solution is used to wash out and improve vision in area. Alternatively an occlusion catheter with an irrigation channel is inserted in opposite direction from treatment catheter for a more exact occlusion and irrigation in vessel-valve area. Next, a radial optical fiber is introduced and placed at post-valve segment. Laser is applied to reduce target segment's diameter. Laser wavelength is preferably around 1470 nm. In other embodiments alternative wavelengths are applied, including but not limited to 1550 nm and 1900 nm. Optical fiber is then retreated to pre-valve segment and laser is applied to reduce this segment's diameter. Next, radial fiber is withdrawn and replaced by an axial optical fiber. Laser energy is applied such that laser sutures are achieved at valve ring. This action greatly restores original shape and diameter of diseased valve and thus restores/rejuvenates its function of retaining retrograde blood flow.

Described technique with present invention allows for a high rate of success in recovery of diseased vessel valves. Since procedure is done under direct vision, with real time monitoring, and with the application of energy with ideal lasing parameters and fiber tip configurations, the method is highly accurate. The probability of recurrence is, thus, very low.

Ideal candidates for mentioned treatment are patients with both deep and superficial insufficiencies. For example, in the deeper veins, the femoral valve and the popliteal valve can be repaired with success. At a more superficial level, the sapheno-femoral and sapheno-popliteal junctions can also benefit from the present invention.

The present invention is further illustrated by the following example, but is not limited thereby:

Example

A deep venous insufficiency is treated by treating the femoral valve, located just under the exit of the deep femoral vein. First of all, there is a preoperative assessment to determine the venous anatomy and the location of valves by means of venography and Doppler ultrasound. Through echography, existence of a treatable valve is determined. Then, diameter is measured and ambulatory venous plethysmography is carried out to determine regurgitation volume, time for recuperation of venous refill and venous refill index. Equipment used for procedure is a laser source capable of emitting at a wavelength of about 1470 nm; 360 degree radial emitting fibers, and axial emitting fibers; ultrasound imaging equipment and direct imaging equipment and a special catheter such as the one described in FIG. 2. Through ultrasound channel of special catheter, a 40 MHz probe is inserted to assess pre and post treatment vessel diameter as well as blood flow through vessel. Seldinger technique is performed with a 4.5 or 6.5 French catheter needle. Catheter is introduced under ultrasound guidance. Next, vessel is washed out clear of blood with transparent non-aqueous solution and cuffs are inflated at distal and proximal portions to prevent further blood flow into the treated portion. Ultrasound imaging is used to determine correct positioning of catheter. Then, laser energy is emitted radially both upstream and downstream with respect to valve position while observing reduction of diameter vein. Next, valve is treated directly by applying laser suture points with axially emitting fiber. Once lasing is done, cuffs are deflated and results are assessed by ultrasound while applying induced valsalva maneuver and anti-trendelembourg positioning of the patient. Finally, prophylactic anticoagulation is applied and Doppler control is carried out to assess procedure success.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A method for repairing a vessel valve with an endoluminal catheter device comprising the steps of:
    a. introducing said catheter device endoluminally through said vessel to the area downstream of the valve,
    b. applying distal and proximal cuffs to occlude blood flow in the area of the valve,
    c. washing the vessel substantially free of blood in the area of the vessel between the cuffs,
    d. inserting a 360° radially emitting optical fiber through the catheter device,
    e. irradiating the post-valve segment of the vessel wall with laser radiation from the 360° radially emitting optical fiber to reduce the diameter of the vessel's inner wall in the post valve segment,
    f. irradiating the pre-valve segment of the vessel wall with laser radiation from the 360° radially emitting optical fiber to reduce the diameter of the vessel's inner wall in the pre valve segment,
    g. replacing the 360° radially emitting optical fiber by an axially emitting optical fiber,
    h. applying laser suture points to the valve ring with the axially emitting optical fiber,
    i. removing the cuffs, and
    j. assessing the irradiation results.

2. The method according to claim 1 wherein said introducing said catheter device is selected from the group consisting of echo-guided puncture according to Seldinger technique and direct venous access.

3. The method according to claim 1 wherein said applying laser radiation is irradiating at a wavelength selected from the group of about 1470±30 nm, about 1550±30 nm and about 1900±50 nm.

4. The method according to claim 1 further comprising the step of irrigating vessel with liquid solution.

5. The method according to claim 1 wherein said evaluating irradiation results is done by ultrasound control.

\* \* \* \* \*